United States Patent [19]

Kaczorowski et al.

[11] Patent Number: 4,604,394
[45] Date of Patent: Aug. 5, 1986

[54] ANTIARRHYTHMIC COMPOSITIONS AND METHOD

[75] Inventors: Gregory J. Kaczorowski, Edison, N.J.; Peter KS. Siegl, Blue Bell, Pa.

[73] Assignee: Merck & Co., Inc., Rahway, N.J.

[21] Appl. No.: 655,777

[22] Filed: Oct. 1, 1984

[51] Int. Cl.$^4$ ............................................ A61K 31/495
[52] U.S. Cl. ...................................... 514/255; 514/821
[58] Field of Search ................. 514/255, 821; 544/407

[56] References Cited

U.S. PATENT DOCUMENTS

| 3,300,494 | 1/1967 | Cragoe | 544/407 |
|---|---|---|---|
| 3,305,552 | 2/1967 | Cragoe et al. | 544/407 |
| 3,313,813 | 4/1967 | Cragoe | 544/407 |
| 3,328,404 | 6/1967 | Pollock et al. | 544/407 |
| 3,491,094 | 1/1970 | Cragoe et al. | 544/407 |
| 4,145,551 | 3/1979 | Cragoe et al. | 544/407 |
| 4,399,138 | 8/1983 | Barlow et al. | 514/255 |

FOREIGN PATENT DOCUMENTS

| EP86564A | 8/1983 | European Pat. Off. | |
| 2733291 | 1/1978 | Fed. Rep. of Germany | 544/407 |
| 96517 | 9/1972 | France | 544/407 |

Primary Examiner—Douglas W. Robinson
Attorney, Agent, or Firm—Alice O. Robertson; Michael C. Sudol, Jr.

[57] ABSTRACT

Pharmaceutical compositions and methods useful in the treatment of cardiac arrhythmias are described.

10 Claims, No Drawings

ANTIARRHYTHMIC COMPOSITIONS AND METHOD

The present invention relates to antiarrhythmic compositions. More particularly, the invention relates to a certain therapeutic pyrazinoylguanidine compositions and their use in treating cardiac arrhythmias.

The therapeutic compositions of the present invention comprise a pyrazinoylguanidine compound as active ingredient in admixture with a pharmaceutically acceptable carrier. The pyrazinoylguanidine compound as herein employed is a compound represented by the formula:

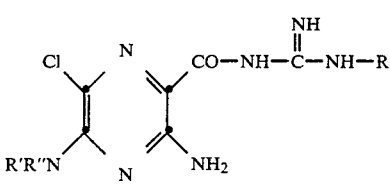

or a pharmaceutically acceptable salt thereof.

In the foregoing and succeeding formulas,
R is hydrogen or $-C_nH_{2n}-Ar$ wherein n is 1 or 2;
R' is hydrogen or lower alkyl; and
R" is hydrogen, lower alkyl, benzyl, substituted benzyl, phenyl or substituted phenyl;
provided that when R is $-C_nH_{2n}-Ar$, R' and R" are hydrogen.

In the above and subsequent formulas, Ar is a substituted phenyl or naphthyl group. Suitable substituents include halo, lower alkyl, lower alkoxy and nitro. By "halo" is meant any of the common halo groups: chloro, bromo, iodo and fluoro. By "lower alkyl" and "lower alkoxy" is meant branched or straight chain groups from 1 to 4 carbon atoms, inclusive. There may be from 1 to 3 substituents, preferably 2, which may be the same or different.

When R' or R" is lower alkyl, the expression "lower alkyl" is meant a straight or branched chain group of from 1 to 4 carbon atoms.

When R" is a substituted phenyl or benzyl group, the group has a single substituent which may be halo, lower alkyl or lower alkoxy, wherein halo, lower alkyl and lower alkoxy have the same scope of meaning as hereinbefore defined.

It is herein noted that the foregoing compounds are generically referred to as pyrazinoylguanidine compounds and although the specific compounds may be named as a (substituted pyrazinoyl)guanidine compound, an alternative nomenclature may be employed in which the compounds are named as a (substituted-pyrazine-2-carbonyl)guanidine compound.

The guanidine compounds have a basic nitrogen group and form acid addition salts. These salts embrace salts of pharmaceutically acceptable acids and include, inter alia, inorganic acids such as the hydrohalic acids (e.g. hydrochloric, hydroiodic and hydrobromic acid), sulfuric acid, sulfamic acid, nitric acid, phosphoric acid, and the like; the organic acids such oxalic, tartaric, citric, lactic, pamoic, fumaric, acetic, maleic, succinic, gluconic, saccharic, p-toluenesulfonic, ascorbic, malic, cinnamic, benzoic and the like acids.

The compositions comprising the pyrazinoylguanidine compounds are desirable antiarrhythmic agents.

Preferred compositions for superior antiarrhythmic properties are compositions in which the pyrazinoylguanidine compound is represented by the formula

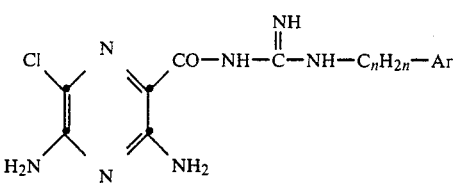

wherein Ar may be represented by

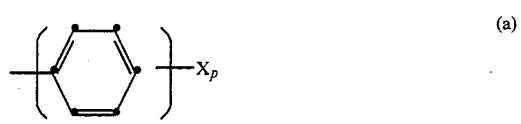

or

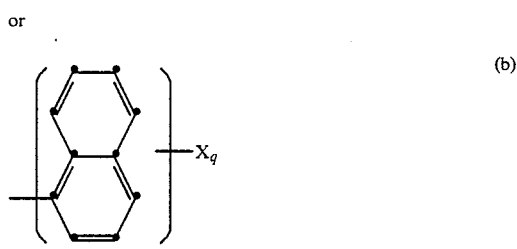

wherein each X independently may be halo, lower alkyl from 1 to 4 carbon atoms, lower alkoxy from 1 to 4 carbon atoms and nitro, and p is from 1 to 3 and q is from 0 to 2.

Most especially preferred are compositions in which the pyrazinoylguanidine compounds are represented by the formula

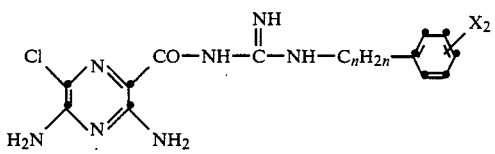

wherein X is as previously defined.

An aspect of the present invention is the provision of an improved method for treating cardiac arrhythmias by administering to a subject in need of such treatment a therapeutically effective amount of a pyrazinoylguanidine compound.

The pyrazinoylguanidine compounds employed as antiarrhythmic agents are generally known compounds or are closely related to known compounds and may be prepared by any of the appropriate methods known to the skilled in the art. Representative methods for preparation may be found in U.S. Pat. No. 3,313,813.

In one method for preparation, a pyrazinoic acid ester having the formula

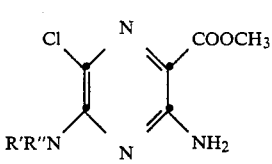

and a guanidine compound having the formula

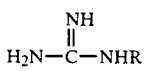

are mixed together at ambient temperature or with heating on a steam bath, with or without a solvent for time sufficient to complete the reaction with the formation of the pyrazinoylguanidine compound, and the product thus obtained thereafter recovered by cooling and triturating with water.

In the above reaction, the ester starting material is illustrated as a methyl ester but since the methyl group is lost as by-product, any ester may be employed. The guanidine compound is usually obtained as the hydrochloride salt and may therefore be converted to the free base just prior to the reaction with the ester by adding the hydrochloride salt to an alcohol solution of sodium, removing the sodium chloride by-product and concentrating the filtrate in vacuo.

The above reaction is preferably carried out by adding the pyrazinoic acid ester to a concentrated solution of the guanidine compound in an alcoholic solvent under anhydrous conditions with heating on a steam bath for from a few minutes to a few hours, thereafter allowing the reaction mixture to cool, then triturating with water to obtain the product. The latter usually separates as a gum and may be purified by forming a salt such as a hydrochloride salt, and thereafter regenerating the base.

When the pyrazinoylguanidine compound is desired as a salt, the base is reached with the appropriate acid in a conventional manner to obtain the desired compound in the salt form.

Alternatively, when the ring amino group is substituted, the following method of preparation may be employed. A (3-amino-5,6-dichloropyrazinoyl)guanidine having the formula

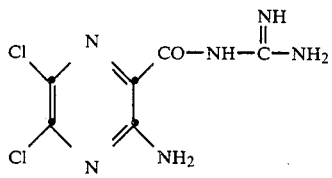

is intimately contacted with an amine represented by

in a solvent such as dimethylformamide, secondary alcohol, tertiary alcohol or dimethylsulfoxide for time sufficient to complete the reaction with the formation of a pyrazinoylquanidine product, and the product thus obtained thereafter recovered from the reaction mixture.

In the above reaction, the starting (3-amino-5,6-dichloropyrazinoyl)guandine may be prepared by reacting guanidine with methyl 3-amino-5,6-dichloropyrazinoate (a known compound obtained by reacting methyl 3-aminopyrazinoate with sulfuryl chloride) by refluxing an alcoholic e.g. isopropyl alcohol solution to obtain the starting substituted guanidine which may be isolated as the hydrochloride and thereafter intimately mixing a solution of said guanidine starting material in a solvent such as dimethylformamide with the appropriate amine R'R"NH. The mixture is generally warmed on a steam both for a few minutes to a few hours to obtain the desired pyrazinoylguanidine product and the product then recovered by diluting with water. The product may be recovered and purified or converted into a salt employing conventional procedures.

The pyrazinoylguanidine compounds of Formula I are adaptable for use as antiarrhythmic agents.

The usefulness of a compound as an antiarrhythmic agent may be demonstrated first in an in vitro test on papillary muscles isolated from the right ventricle of guinea pig hearts. In this operation, the muscles are prepared for testing by suspending in a 20 milliliter organ bath containing Krebs-Hensleit solution at 37° C. and the bath aerated with a 95% oxygen/carbon dioxide mixture. The muscles are then electrically paced at 1 Hz by means of a bipolar platinum electrode and stimulated with a stimulator with a 120% threshold voltage for 1 millisecond and the isometric tension recorded with a transducing cell. The test compounds are introduced into the tissue baths to provide desired test concentration. Then to each bath ouabain is introduced to provide a ouabain concentration of $10^{-6}$ to $10^{-5}$M, and the time required to the onset of arrhythmia determined. Compounds capable of demonstrating protective activity for a period of time approaching 15 minutes or more are considered to be potentially useful as a therapeutic agent. The antiarrhythmic property is demonstrated by the ability of the compounds to markedly decrease fibrillation induced in laboratory animals such as anesthetized dogs.

One way this property may be demonstrated is by pretreating a dog with the test compound, thereafter producing a severe multifocal ventricular arrhythmia, by injecting a sclerosing agent, 1,1,2,3,4,4-hexachloro-1,2,3,4-tetrafluorobutane into the anterior descending branch of the left coronary artery and determining the effectiveness of the test compound in maintaining the normalcy of the heartbeat from electrocardiogram (ECG) readings.

In carrying out this operation, dogs weighing 6 to 10 kilograms are employed. Each dog is anesthetized with vinbarbital sodium and while ascertaining the body temperature remains at 37° C., an endotracheal tube is inserted into the trachea and the dog artificially respired with room air. The vagus nerves are left intact. The test compound then is administered through a catheter inserted into the femoral artery and an electrocardiogram (Lead II) recorded. A left thoracotomy is performed to expose the anterior descending branch of the left coronary artery, and the artery then injected with a sclerosing agent at a volume of 3.5 μl/kg to produce infarction. Twenty minutes prior to infarction, the dog is given mecamylamine at a rate of 1 mg/kg intravenously to achieve a more uniform preinfarction heart rate. Electrocardiogram is recorded for 5 seconds every 2 minutes. The number of electrical impulses recorded during each 5-second interval is designated "Total" and the number of normal ECG patterns for each interval is designated "Normal". Averages of Total and Normal are made for each 10-minute interval and the averages at each interval are multiplied by 2.4 to obtain rate per minute. Antiarrhythmic efficacy is indicated by a greater percent of normal Lead II ECG complexes during the arrhythmic period.

Another way this property may be demonstrated is by the effectiveness of the compounds against ouabain induced ventricular tachycardia. In such demonstration, the test compounds are introduced into the artery after the onset of arrhythmia to determine the reduction of ectopic beats.

In carrying out this procedure, dog weighing 6 to 10 kilograms are initially anesthetized with sodium pentabarbital with supplemental administration of anesthetic as needed to maintain the aortic pressure between 100/60 and 150/100. In each dog, a cuffed endotracheal tube is inserted into the trachea and the animal allowed to breathe spontaneously while the body temperature is maintained at 37° C. A saline-filled catheter is inserted into the lower abdominal aorta and bilateral vagotomy is performed. A ligature is placed around the right vagus nerve trunk and a bipolar electrode attached to the nerve's distal stump which has been covered with mineral oil. The electrode is attached to a nerve stimulator to deliver 2 millisecond pulses for 5 seconds with a pulse-pulse interval of 25 microseconds. A provision is made for an electrocardiogram and readings are made at 5-minute intervals. After a 15-minute stabilization period following surgery, a control demonstration is made with observation of ECG for 10 seconds followed by determination of a setting for producing sinus arrest with 5 seconds stimulation. Ouabain octahydrate is infused intravenously at an initial dose of 40 μg/kg to induce ventricular tachycardia, and after 30 minutes vagal stimulation administered for 5 seconds. The procedure is repeated as necessary to induce ouabain arrhythmia. 30 minutes after the onset ouabain arrhythmia, readings of ECG are obtained for a 10-second period every 5 minutes. The test drug is injected intravenously 30 minutes after the onset of ouabain arrhythmia and observations made for 30 minutes with readings taken every 5 seconds. After 15 seconds, an additional 2.5 mg per kg amount of the test compounds are administered to provide a cumulative dose.

The process of this invention comprises internally administering to subjects with cardiac arrhythmia a therapeutically effective amount of a pyrazinoylguanidine compound intimately admixed with a pharmaceutically acceptable carrier. Preferably, the compound is administered in a dosage range of from about 0.5 milligram to about 100 milligrams. When the administration is to be carried out orally, the amount is preferably from about 25 to about 100 milligrams. When the administration is to be intravenous, the amount is in the range of from about 0.5 milligram to 10 milligrams. The process embraces the administration of the hereinafter described dosage unit form to subjects for antiarrhythmic purposes.

To prepare the pharmaceutical compositions of this invention, the pyrazinoylguanidine compounds of Formula I are combined in intimate admixture with a pharmaceutically acceptable carrier which may take a wide variety of forms depending of the form of preparation desired for administration, i.e., oral or parenteral. In preparing the compositions in oral dosage forms, any of the usual pharmaceutical media may be employed, such as for example, water, glycols, oils, alcohols and the like for oral liquid preparations such as suspensions, elixirs, solutions; or starches, sugars, kaolin, lubricants, binders, disintegrating agents and other solid carriers for oral solid preparations such as powders, capsules, and tablets. Because of their ease in administration, tablets and capsules represent the most advantageous oral dosage form. Since this is so, solid pharmaceutical carriers are preferred. For parenteral injection, the carrier will usually comprise sterile water, at least in part, although other ingredients such as materials to aid in the solubility may be included. Injectable solutions, for example, may be prepared in which the carrier comprises saline solution, glucose solution or a mixture or saline and glucose solution. Injectable suspensions may also be prepared in liquid carriers together with suspending agents and the like.

It is especially advantageous to formulate the aforementioned pharmaceutical compositions in dosage unit form for ease of administration and uniformity of dosage. Dosage unit form as used in the specification and claims herein refer to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonsful, and the like, and segregated multiples thereof. The amount of active ingredient per dosage unit is from about 5 milligrams to about 10 milligrams.

The following examples illustrate the invention but are not to be construed as limiting.

EXAMPLE I

Papillary muscles isolated from the right ventricle of guinea pig hearts were prepared for testing by suspending in a 20 milliliter organ bath containing Krebs-Hensleit solution at 37° C. and the bath aerated with a 95% oxygen/5% carbon dioxide mixture. The muscles were electrically paced at 1 Hz by means of a bipolar platinum electrode and stimulated with a stimulator with 120% threshold voltage for 1 millisecond and isometric tension recorded with a transducing cell.

In separate operations, 1-(3,5-diamino-6-chloropyrazine-2-carbonyl)-3-(3,4-dichlorobenzyl)-guanidine (DCB) was introduced into several tissue baths to provide concentrations of 10 μM (micromolar), 20 μM and 40 μM. Other baths contained only vehicle. To each bath, ouabain was introduced to provide ouabain concentration therein of $10^{-6}$M and the time required to the onset of arrhythmia was determined. The results are seen in Table I.

TABLE I

| Concentration of DCB | Number of Tissue Samples | Time to Arrhythmia Mean ± 1 S.D. | Number Protective over 15 Minutes |
|---|---|---|---|
| 40 μM | 12 | 13.16 ± 2.55 | 7 |
| 20 μM | 6 | 10.25 ± 3.10 | 1 |
| 10 μM | 5 | 8.43 ± 3.30 | 0 |
| Control (Vehicle) | 7 | 4.61 ± 2.40 | 0 |

0.4 milliliter dimethylsulfoxide + 1 to 2 drops isethionate and q.s. to 2.5 milliliters with distilled water.

EXAMPLE II

Guinea pig papillary muscles were prepared as described in Example I.

In separate operations test compounds were introduced into the tissue baths to provide a concentration therein of 40 μM and the tissues incubated in 60 minutes. Ouabain was introduced into these baths and to a control bath in which the tissues were immersed only in the vehicle to provide a ouabain concentration therein of $10^{-5}$M. Following the introduction of ouabain, the time to onset of arrhythmia was determined. Untreated tissues developed arrhythmia in 3 to 5 minutes. Compounds were considered active when the time for onset of arrhythmia was greater than the time for onset of arrhythmia in control or vehicle treated tissues. The results are seen in Table II.

TABLE II

| Compound | Time to Arrhythmia Minutes X ± S.D. | Fraction Having Protective Activity greater than 15 minutes |
|---|---|---|
| 1-(3,5-Diamino-6-chloropyrazine-2-carbonyl)-3-(o-chlorobenzyl)-guanidine | +15 | 3/3 |
| 1-(3,5-Diamino-6-chloropyrazine-2-carbonyl)-3-(3,4-di-chlorobenzyl)guanidine | 13.16 ± 2.55 | 7/12 |
| 1-(3,5-Diamino-6-chloropyrazine-2-carbonyl)-(2,4-di-methyl-benzyl)guanidine | 14.71 ± 0.51 | 2/3 |
| 1-(3,5-Diamino-6-chloropyrazine-2-carbonyl)-3-(1-naphthyl-methyl)guanidine | 13.90 ± 2.20 | 3/4 |
| 1-(3,5-Diamino-6-chloropyrazine-2-carbonyl)-3-benzylguanidine | 8.14 ± 3.98 | 1/7 |
| 1-(3-Amino-6-chloro-5-(p-chlorobenzyl-amino)pyrazine-2-carbonyl)guanidine | 8.98 ± 1.16 | 0/3 |
| 1-(3-Amino-6-chloro-5-(N—propylbutyl-amino)pyrazine-2-carbonyl)guanidine | 7.70 ± 2.29 | 0/3 |
| Vehicle | 3.42 ± 1.60 | 0/6 |

EXAMPLE III

In separately conducted operations, 11 dogs weighing 6 to 10 kilograms were initially anesthetized with sodium pentabarbital with supplemental administration of anesthetic as required to maintain aortic pressure between 100/60 and 150/100. For each animal, a cuffed endotracheal tube was inserted into the trachea and the animal allowed to breath spontaneously while the body was maintained at 37° C. A saline-filled catheter was inserted in the lower abdominal aorta and a bilateral vagotomy performed. A ligature was placed around the right vagus nerve trunk and a bipolar electrode was attached to the nerve's distal stump which previously had been covered with mineral oil and the electrode attached to a nerve stimulator to deliver 2 millisecond pulses for 5 seconds with pulse-pulse interval of 25 milliseconds. Provisions were made for electrocardiogram and readings made at 5-minute intervals.

After a stabilization period following surgical procedures, a control demonstration was made with observation of ECG for 10 seconds followed by determination of stimulation parameters for producing sinus arrest with 5 seconds of vagal stimulation.

Ouabain octahydrate was infused intravenously at an initial dose of 40 g/kg to induce ventricular tachycardia and after 30 minutes, vagal stimulation administered for 5 seconds. The procedure was repeated as necessary to induce ouabain arrhythmia. 30 minutes after the onset of ouabain arrhythmia, readings of ECG were obtained for a 10 second period every 5 minutes. Test drugs 1-(3,5-diamino-6-chloropyrazine-2-carbonyl)-3-(3,4-dichlorobenzyl)guanidine and 1-(3,5-diamino-6-chloropyrazine-2-carbonyl)guanidine were injected at a dose of 1 mg/kg intravenously 30 minutes after the onset of ouabain arrhythmia and observed for 30 minutes with readings taken every 5 minutes. After 15 minutes, an additional 2.5 mg/kg amount of the test drugs were administered to provide a cumulative dose of 3.5 mg/kg.

The ectopic beats (beats located away from the normal position) and the total beats were determined from ECG, and the percent ectopy calculated. The effectiveness is indicated by a decrease in the percent ectopy. The results are seen in Table III.

TABLE III

| | | | Percent Ectopy $\frac{\text{Ectopic beats}}{\text{Total beats}} \times 100$ | | | |
|---|---|---|---|---|---|---|
| | | 30 Minute | Admin. of 1 mg/kg | | Test Compound 3.5 mg/kg | |
| Test Compound | No. of Dogs | Arrhythmia* | 5 min | 15 min. | 5 min. | 15 min. |
| 1-(3,5-Diamino-6-chloro-pyrazine-2-carbonyl)-3-(3,4-di-chlorobenzyl)-guanidine | 7 | 93 ± 4 | 83 ± 15 | 40 ± 20 | 58 ± 19 | 42 ± 3 |
| 1-(3,5-Diamino-6-chloro-pyrazine-2-carbonyl)-guanidine | 4 | 99 ± 1 | 100 ± 0 | 97 ± 4 | 97 ± 3 | 99 ± 2 |

*Prior to administration of test compound

EXAMPLE IV

In separately conducted operations, dogs weighing 6 to 10 kilograms were anesthetized with vinbarbital sodium and the body temperature maintained at 37° C. In each dog, a endotracheal tube was inserted into the trachea and the dog artificially respired with room air. The vagus nerves were left intact. The test compounds were administered through a catheter inserted into the femoral artery. Electrocardiograms (Lead II) were recorded.

In each dog, a left thoracotomy was performed to expose the anterior descending branch of the left coronary artery and the artery injected with a sclerosing agent, 1,2,3,4,4-hexachloro-1,2,3,4-tetrafluorobutane at a volume of 3.5 μl/kg. Twenty minutes prior to infarction, the dogs were given mecamylamine (1.0 mg/kg i.v.) to achieve more uniform preinfarction heart rates. The ECGs were recorded for 5 seconds every 2 minutes (30 segment during 60 minutes). The number of electrical impulses recorded during each 5-second interval were designated "Total" and the number of normal ECG patterns for each interval were designated "Normal". Averages of "Total" and "Normal" were made for each 10-minute interval and the averages at each interval were multiplied by 2.4 to obtain rate per minute. Antiarrhythmic efficacy is indicated by a greater of normal Lead II ECG complexes during the arrhythmic period. At the termination of each operation, the heart was removed to establish myocardial damage thereby certifying that the sclerosing agent was injected into the artery. Data from those not showing myocardial damage were not employed. The results are seen in Table IV.

TABLE IV

| Test Compound | Rate of Administration | Number of Animals | Average Percent Normal ECG Complexes |
|---|---|---|---|
| 1-(3,5-Diamino-6-chloropyrazine-2-carbonyl)-3-(3,4-dichlorobenzyl)-guanidine | 1.25 mg/kg | 3 | 24 ± 6 |
| 1-(3,5-Diamino-6-chloropyrazine-2-carbonyl)-3-(3,4-dichlorobenzyl)-guanidine | 2.5 mg/kg | 4 | 70 ± 15 |
| 1-(3,5-Diamino-6-chloropyrazine-2-carbonyl)-3-(3,4-dichlorobenzyl)-guanidine | 5.0 mg/kg | 3 | 78 ± 15 |
| 1-(3,5-Diamino-6-chloropyrazine-2-carbonyl)-3-benzyl-guanidine | 1.25 mg/kg | 3 | 58 ± 12 |
| 1-(3,5-Diamino-6-chloropyrazine-2-carbonyl)-3-benzyl-guanidine | 2.5 mg/kg | 3 | 74 ± 13 |
| 1-(3,5-Diamino-6-chloropyrazine-2-carbonyl)guanidine | 2.5 mg/kg | 3 | 43 ± 11 |
| Lidocaine | 0.25 mg/kg/min | 2 | 89 ± 10 |
| Control | — | 4 | 20 ± 9 |

EXAMPLE V 1000 hard gelatin capsules, each containing 50 milligrams of 1-(3,5-diamino-6-chloropyrazine-2-carbonyl)-3-(3,4-dichlorobenzyl)guanidine (DCB) are prepared from the following formulation:

| Component | Weight in grams |
|---|---|
| DCB | 50 |
| Starch | 250 |
| Lactose | 750 |
| Talc | 250 |
| Calcium Stearate | 10 |

A uniform mixture of the ingredients is prepared by blending, and used to fill two-piece hard gelatin capsules. The capsules are suitable to be used for treating arrhythmia.

EXAMPLE VI

Similar capsules are prepared in separate operations in which the compounds listed in the following table are substituted for the 1-(3,5-diamino-6-chloropyrazine-2-carbonyl)-3-(3,4-dichlorobenzyl)-guanidine in Example VI.

TABLE $$\text{Cl} \diagdown \text{N} \diagup \text{CO-NH-C(=NH)-NH-R}$$
$$\text{R'R''N} \diagup \text{N} \diagdown \text{NH}_2$$

| R' | R'' | R |
|---|---|---|
| H | H | —CH$_2$—C$_6$H$_4$—4-CH$_3$ |
| H | H | —CH$_2$—C$_6$H$_5$ |
| H | H | —CH$_2$—C$_6$H$_4$—2-Cl |
| H | H | —CH$_2$—C$_6$H$_4$—4-OCH$_3$ |
| H | H | —CH$_2$—C$_6$H$_3$—2,4-(CH$_3$)$_2$ |
| H | H | —CH$_2$—C$_6$H$_3$—2,4-Cl$_2$ |
| H | H | —CH$_2$—CH$_2$—C$_6$H$_5$ |
| CH$_3$— | H | H |
| C$_2$H$_5$— | H | H |
| CH$_3$(CH$_2$)$_2$— | H | H |
| (CH$_3$)$_2$CH— | H | H |
| CH$_3$(CH$_2$)$_3$— | H | H |
| (CH$_3$)$_2$CHCH$_2$— | H | H |
| (CH$_3$)$_3$C— | H | H |
| C$_6$H$_5$—CH$_2$— | H | H |
| 4-CH$_3$—C$_6$H$_4$—CH$_2$— | H | H |
| 2-F—C$_6$H$_4$—CH$_2$— | H | H |
| 4-Cl—C$_6$H$_4$CH$_2$ | H | H |
| C$_6$H$_5$—CH$_2$—CH$_2$— | H | H |
| C$_6$H$_5$— | H | H |
| 4Cl—C$_6$H$_5$ | H | H |
| CH$_3$— | CH$_3$— | H |
| C$_2$H$_5$ | CH$_3$ | H |
| CH$_3$(CH$_2$)$_2$ | CH$_3$ | H |
| (CH$_3$)$_2$CH | CH$_3$ | H |
| (CH$_3$)$_2$CH | CH$_3$(CH$_2$)$_3$— | H |
| CH$_3$(CH$_2$)$_3$— | CH$_3$(CH$_2$)$_3$— | H |
| C$_2$H$_5$ | C$_2$H$_5$ | H |
| CH$_5$— | CH$_3$— | H |
| C$_6$H$_5$CH$_2$— | CH$_3$— | H |

EXAMPLE VII 2000 compressed tablets, each containing 50 milligrams of DCB are prepared from the following formulation

| Component | Grams |
|---|---|
| DCB | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

What is claimed is:

1. A method for treating cardiac arrhythmias which comprises administering to a subject in need of such treatment, a therapeutically effective amount of a pyrazinoylguanidine compound of the formula $$\text{Cl} \diagdown \text{N} \diagup \text{CO-NH-C(=NH)-NH-C}_n\text{H}_{2n}\text{-Ar'}$$
$$\text{H}_2\text{N} \diagup \text{N} \diagdown \text{NH}_2$$

wherein Ar' may be represented by:

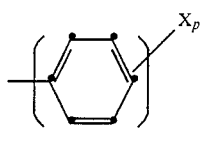 (i)

or

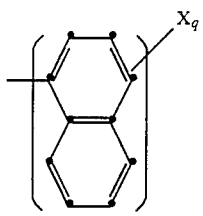 (ii)

wherein each X independently may be halo, lower alkyl, lower alkoxy and nitro, p is from 1 to 3 and q is from 0 to 2; and wherein n is from 1 to 2; or pharmaceutically acceptable salts thereof.

2. A method according to claim 1 wherein said pyrazinoylguanidine compound is administered in a therapeutically effective amount in the range of from about 0.5 milligram to 100 milligrams.

3. A method according to claim 2 wherein said pyrazinoylguanidine compound is administered orally in an amount of from about 25 to 100 milligrams.

4. A method according to claim 2 wherein said pyrazinoylguanidine compound is administered intravenously in an amount of from about 0.5 milligram to 10 milligrams.

5. A method according to claim 1 wherein Ar is

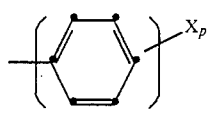

6. A method according to claim 1 wherein Ar is

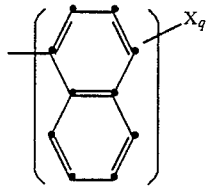

7. The method of claim 1 wherein the pyrazinoylguanidine compound is 1-(3,5-diamino-6-chloropyrazine-2-carbonyl)-3-(3,4-dichlorobenzyl)guanidine.

8. The method of claim 1 wherein the pyrazinoylguanidine compound is 1-(3,5-diamino-6-chloropyrazine-2-carbonyl)-3-(o-chlorobenzyl)guanidine.

9. The method of claim 1 wherein the pyrazinoylguanidine compound is 1-(3,5-diamino-6-chloropyrazine-2-carbonyl)-3-(2,4-dimethylbenzyl)guanidine.

10. The method of claim 1 wherein the pyrazinoylguanidine compound is 1-(3,5-diamino-6-chloropyrazine-2-carbonyl)-3-(1-naphthylmethyl)guanidine.

* * * * *